United States Patent [19]

Kubbota et al.

[11] Patent Number: 5,106,989
[45] Date of Patent: Apr. 21, 1992

[54] ALKYL-SUBSTITUTED 2,2'-(1,4-NAPHTHALENEDIYL)DIBENZOXAZOLE AND PHOTOGRAPHIC SUPPORT COMPRISING THE SAME

[75] Inventors: Massashi Kubbota, Misato; Touru Noda, Matsudo, both of Japan; Isao Kawakami, Machida, all of Japan

[73] Assignees: Mitsubishi Paper Mills Limited; Mitsubishi Kasei Corporation, both of Tokyo, Japan

[21] Appl. No.: 422,799

[22] Filed: Oct. 18, 1989

[30] Foreign Application Priority Data

Oct. 20, 1988 [JP] Japan .................. 63-265052

[51] Int. Cl.$^5$ .......................... C07D 263/64
[52] U.S. Cl. .................. 548/220; 430/512; 428/512
[58] Field of Search ...................... 548/220

[56] References Cited

U.S. PATENT DOCUMENTS

| | | | |
|---|---|---|---|
| 3,135,762 | 2/1964 | Maeder et al. | 548/220 |
| 3,336,330 | 6/1967 | Schinzel | 548/220 |
| 3,501,298 | 3/1970 | Crawfeld . | |
| 3,641,044 | 2/1972 | Matter et al. | 548/220 |
| 4,110,246 | 8/1978 | Frischkorn | 548/220 |
| 4,791,205 | 12/1988 | Schinzel | 548/220 |
| 4,794,071 | 12/1988 | Tomko . | |
| 4,847,149 | 7/1989 | Kiyohara | 548/220 |

FOREIGN PATENT DOCUMENTS

| | | |
|---|---|---|
| 1282592 | 7/1969 | Fed. Rep. of Germany . |
| 2645301 | 4/1977 | Fed. Rep. of Germany . |
| 2750947 | 5/1979 | Fed. Rep. of Germany . |
| 48-114341 | 6/1975 | Japan . |
| 48-6080 | 5/1976 | Japan . |
| 51-15865 | 5/1976 | Japan . |
| 56-51336 | 12/1981 | Japan . |

OTHER PUBLICATIONS

Gugielmetti, Chem. Abstr, vol. 94, entry 48840s (1981).
Frischkorn, Chem. Abstr, vol. 71, entry 126003n (1969).
Gugielmetti, Chem. Abstr, vol. 87, entry 68338t (1977).

Primary Examiner—Donald G. Daus
Attorney, Agent, or Firm—Cushman, Darby & Cushman

[57] ABSTRACT

An alkyl-substituted 2,2'-(1,4-naphthalenediyl)dibenzoxazole represented by the structural formula [I]:

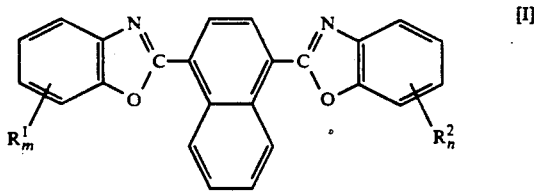

wherein $R^1$ and $R^2$ are independently alkyl groups having 9–20 carbon atoms, m and n are independently 0 or positive integers and m+n=1–4, and a photographic support comprising the alkyl-substituted 2,2'-(1,4-naphthalenediyl)dibenzoxazole as a fluorescent agent. The photographic support comprising the same has bright whiteness and does not cause color change or bleeding out.

5 Claims, No Drawings

ALKYL-SUBSTITUTED 2,2'-(1,4-NAPHTHALENEDIYL)DIBENZOXAZOLE AND PHOTOGRAPHIC SUPPORT COMPRISING THE SAME

This invention relates to a novel alkyl-substituted 2,2'-(1,4-naphthalenediyl)benzoxazole and a photographic support comprising the same as a fluorescent agent. Particularly, this invention relates to a photographic support comprising a sheet as a substrate and a polyolefin resin with which both sides of the sheet are coated, the side of the photographic support where images are to be formed (hereinafter referred to as the image-forming side) having improved whiteness. More particularly, this invention relates to a resin-coated sheet type photographic support, the tendency of which to have yellowness caused by titanium dioxide, especially rutile type titanium dioxide pigment much contained in the resin layer on the image-forming side is reduced by adding a specific fluorescent agent to the resin layer, whereby the whiteness is improved.

Recently, as a photographic support, a water-resistant support has been mainly used which comprises highly sized base paper or water-resistant film and polyolefin resin such as polyethylene with which both sides of the base paper are coated, because the water-resistant support coated with the resin meets the requirement that the development should be done automatically and rapidly.

However, the resin-coated sheet type photographic support contains titanium dioxide in the image-forming side to improve photographic properties such as sharpness of images and the like. The titanium dioxide tends to have yellowness and the whiteness of the white ground of photographic images is not sufficient as such.

Especially, for color photographic paper widely used have been required high fidelity and vividness of colors in these days. Therefore, the photographic support is required to have clear whiteness without visual coloration.

On the other hand, an improvement of sharpness of color and monochrome images has been strongly desired, so that the amount of titanium dioxide in the resin layer on the image-forming side tends to become larger still more. Thus, techniques to improve the visual whiteness have been more important.

Heretofore, there have been known several techniques to improve the whiteness of the resin layer containing titanium dioxide on the image-forming side of the resin-coated sheet type photographic support.

For example, U.S. Pat. No. 3,501,298 discloses adding, to the resin layer, a blue inorganic pigment such as ultramarine blue, cobalt blue or the like; a red inorganic pigment such as oxidized cobalt phosphate (e.g. Raspberry V-6260, a trade name of Ferro Colors Corp.); a red organic pigment such as quinacridone red; and a fluorescent whitening agent having a bis(alkyl-substituted benzoxazolyl)thiophene structure such as Uvitex OB (a trade name of Ciba-Geigy Corp.) in addition to titanium dioxide. Japanese Patent Application Kokai No. 53-19021 discloses adding, to the resin layer, a blue inorganic pigment such as ultramarine blue; or a red inorganic pigment such as Daiichi Pink (e.g. DP-1) or Daiichi Violet (e.g. DV-1) (these are manufactured by Daiichi Kasei Kogyo K.K.). Japanese Patent Application Kokoku No. 56-51336 discloses adding, to the resin layer, a fluorescent whitening agent having a bis(benzoxazolyl)naphthalene structure which is unsubstituted or substituted symmetrically by alkyl groups having 1-5 carbon atoms. Japanese Patent Application Kokai No. 61-75341 discloses adding, to the resin layer, a quinacridonic red organic pigment. However, these techniques have the following disadvantages:

In the case of adding an organic or inorganic color pigment to the resin layer on the image-forming side of the resin-coated sheet type photographic support to reduce the tendency that the resin layer has yellowness caused by titanium dioxide much contained therein and improve the visual whiteness, the resin layer is made apparently white by coloring it, and hence, the brightness is lowered and no clear whiteness can be obtained.

Especially, when inorganic pigments are used, they generally contain much moisture, so it follows that the much moisture is taken into the resin layer. When the moisture content becomes large in the resin layer, a crack of the resin layer tends to be caused by blowing up of steam in the step of coating by melt extrusion. Moreover, ultramarine blue and cobalt-based inorganic pigments lower the heat-resistance of the resin on acount of their chemical activity, and consequently the tendency is increased that the degraded resin components stick to the die lip opening of the extrusion coater and are accumulated thereon to grow in the form of an icicle. The accumulated components sticking to and hanging down from the opening cause stringy flaws on the resin layer and remarkably damage the commercial value of the resin-coated sheet type photographic support.

On the other hand, in the case of adding conventional fluorescent whitening agents such as (thiophenediyl)dibenzoxazole and the like to the resin layer to improve the whiteness, the fluorescent whitening agents tend to bleed out from the resin. Thus, neither sufficient stability of color nor sufficient adhesion to photographic emulsion layer can be obtained. Additionally, in the case of adding the conventional fluorescent whitening agents to the resin layer to improve the apparent whiteness, the stability of whiteness is inferior and the resin layer is also inferior in weather resistance such as light resistance, discoloration in darkness or the like. Thus, the resin layer becomes gradually yellow with the lapse of time. Furthermore, in the case of adding a fluorescent whitening agent having an alkyl-substituted (thiophenediyl)dibenzoxazole structure such as Uvitex OB to the resin layer of the resin-coated sheet, the whiteness is not improved and conversely, the yellowness becomes conspicuous when the photographic material comprising the coated paper as a support is treated with an acidic hardening fixing solution.

On the other hand, branched octyl-substituted 2,2'-(1,4-naphthalenediyl)dibenzoxazole is disclosed in Liebigs, Ann. Chem., 1982, 1423-1433 which states the spectroscopic properties obtained by modifying a part of the structure of 2,2'-(1,4-naphthalenediyl)dibenzoxazole used as a fluorescent agent. However, 2,2'-(1,4-naphthalenediyl)dibenzoxazoles substituted by an alkyl group having 9 or more carbon atoms have not been known. Furthermore, in this reference, the serious problem is not disclosed that the fluorescent agent bleeds out from the polyolefin. And it has been unknown that 2,2'-(1,4-naphthalenediyl)dibenzoxazoles substituted by an alkyl group having 9 or more carbon atoms are very advantageous in view of the prevention of bleeding-out.

Therefore, it is an object of this invention to provide a novel alkyl-substituted 2,2'-(1,4-naphthalenediyl)-dibenzoxazole which gives high whiteness when it is added to the resin layer on the image-forming side of a photographic support.

Another object of this invention is to provide a resin-coated sheet type photographic support, which has high brightness and clear whiteness free from visual coloring by reducing the yellowness caused by titanium dioxide contained in a large amount in the resin layer.

A further object of this invention is to provide a resin-coated sheet type photographic support which does not cause resin cracks or bleeding out phenomenon, is excellent in heat resistance, weather resistance and the like, has good preservability of the whiteness, is not yellowed by a photographic treatment solution, and has high brightness and clear whiteness.

A still further object of this invention to provide a resin-coated sheet type photographic support which is excellent in sharpness and resolving power and has high brightness and clear whiteness.

The present inventors have made extensive research in order to solve the above-mentioned problems. As a result, it has been found that the objects of this invention are attained by using a photographic support comprising a sheet and a polyolefin resin with which both sides of the sheet are coated, in which a titanium dioxide pigment and a novel alkyl-substituted 2,2'-(1,4-naphthalenediyl)dibenzoxazole is contained in the resin layer on the image-forming side.

According to this invention, there is provided an alkyl-substituted 2,2'-(1,4-naphthalenediyl)dibenzoxazole represented by the structural formula [I]:

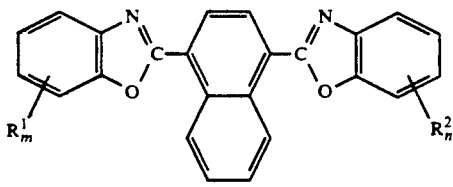

wherein $R^1$ and $R^2$ are independently alkyl groups having 9-20 carbon atoms, m and n are independently 0 or positive integers and $m+n=1-4$.

This invention further provides a photographic support comprising a sheet and a polyolefin resin with which both sides of the sheet is coated, in which a titanium dioxide pigment and a fluorescent agent represented by the structural formula [I] is contained in the resin layer on the side of the photographic support where images are to be formed.

In the fluorescent agent represented by the structural formula [I] contained in the photographic support of this invention, $R^1$ and $R^2$ are independently alkyl groups having 9-20 carbon atoms, preferably alkyl groups having 9-16 carbon atoms. Furthermore, $R^1$ and $R^2$ are preferably identical with each other. On the other hand, m and n are, preferably identical with each other, more preferably 1. Though the substituted positions of $R^1$ and $R^2$ are not critical, they are preferably the 5- or 7-positions of the benzoxazole ring.

The compound represented by the structural formula [I] includes, specifically, 2-[4-(2-benzoxazolyl)-1-naphthalenyl]-5-nonylbenzoxazole [II], 2,2'-(1,4-naphthalenediyl)-bis(5-nonylbenzoxazole) [III], 2,2'-(1,4-naphthalenediyl)-bis(5-decylbenzoxazole) [IV], 2,2'-(1,4-naphthalenediyl)-bis(5-dodecylbenzoxazole) [V], 2,2'-(1,4-naphthalenediyl)-bis(5-hexadecylbenzoxazole) [VI], 2-[4-(2-benzoxazolyl)-1-naphthalenyl]-7-decylbenzoxazole [VII], 2,2'-(1,4-naphthalenediyl)bis(7-nonylbenzoxazole) [VIII], 2,2'-(1,4-naphthalenediyl)bis(7-decylbenzoxazole) [IX], 2,2'-(1,4-naphthalenediyl)bis(7-dodecylbenzoxazole) [X] and the like.

In view of the prevention of the bleeding-out phenomenon, it is preferable that both m and n are 1 and $R^1$ and $R^2$ are identical with each other.

The alkyl-substituted 2,2'-(1,4-naphthalenediyl)-dibenzoxazole in which $R^1$ and $R^2$ are identical with each other and m and n are 1 or 2 is prepared by, for example, the following method:

An alkyl-substituted phenol represented by the structural formula (1):

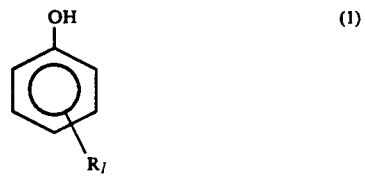

wherein R represents an alkyl group having 9-20 carbon atoms, l represents 1 or 2 is nitrated to produce an alkyl-substituted nitrophenol represented by the structural formula (2):

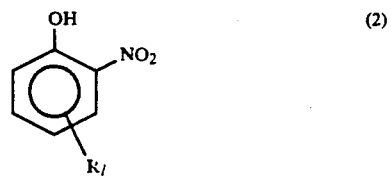

wherein R and l are as defined above.

The nitration of the alkyl-substituted phenol is carried out according to a conventional nitration method, for example, by allowing nitric acid to act in acetic acid. After the reaction, the product is extracted with water and, if necessary, isolated by a chromatography to obtain the compound of the formula (2).

The nitro group of the alkyl-substituted nitrophenol represented by the formula (2) thus-obtained is reduced to obtain an alkyl-substituted aminophenol represented by the formula (3):

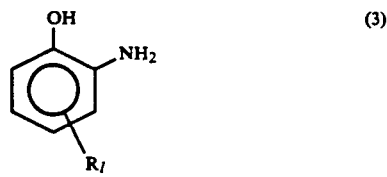

wherein R and l are as defined above.

The reduction of the nitro group is carried out according to a conventional method. For example, there are employed a method of the stoichiometric reduction with iron powder or tin and a catalytic method using Raney nickel or palladium as a catalyst. After the reaction, the solvent is distilled off to obtain the compound of the formula (3).

The alkyl-substituted aminophenol represented by the formula (3) thus-obtained is cyclized by condensation with naphthalene-1,4-dicarboxylic acid in the presence of a condensing agent, or alternatively reacted with naphthalene-1,4-dicarboxylic dichloride to produce an amide compound followed by condensation-cyclization to obtain the alkyl-substituted 2,2'-(1,4-naphthalenediyl)dibenzoxazole represented by the structural formula [I'].

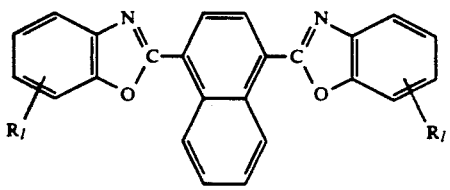

As the condensing agent, polyphosphoric acid is employed in an amount of 5 equivalents or more per equivalent of the compound of the formula (3).

The reaction with an acid chloride is carried out in the presence of a base or an amine such as dimethylaniline. The amine is employed in an amount of one equivalent or more per equivalent of the compound of the formula (3).

The condensation reaction is carried out at a temperature of 150°-280° C. After the reaction, the product is hydrolyzed, extracted and, if necessary, isolated by a chromatography to obtain the objective alkyl-substituted 2,2'-(1,4-naphthalenediyl)dibenzoxazole.

The present compound represented by the structural formula [I'] has a symmetric structure because it is synthesized from one benzoxazole-ring precursor and one naphthalene derivative. However, when the reaction is carried out in the same way using two or more kinds of compounds as the benzoxazole precursors represented by the formula (3) (in this case, l is m or n), a mixture of symmetric type and antisymmetric type is obtained depending upon the probability of each reaction. This mixture is used as a fluorescent agent for a photographic support as it is or after each component has been isolated therefrom.

The photographic support of this invention is described below.

In the resin-coated sheet type photographic support which is one of the objects of this invention, it is preferable that a rutile type titanium dioxide pigment and a fluorescent agent represented by the structural formula [I] is contained in the resin layer on the image-forming side. Though a conventional resin-coated sheet type photographic support containing rutile type titanium dioxide pigment is superior in sharpness and resolving power to one containing anatase type titanium dioxide, it has strong yellowness caused by the titanium dioxide and is not excellent in whiteness. However, this invention makes it possible to provide a resin-coated sheet type photographic support which is excellent in sharpness and resolving power and free of the disadvantages mentioned above, and has high brightness and clear whiteness.

Though the titanium dioxide pigment used in this invention may be of the rutile type or the anatase type, the rutile type titanium dioxide pigment is preferred in view of the sharpness and resolving power. As shown in Japanese Patent Application Kokoku No. 56-5987, the rutile type titanium dioxide pigment and the anatase type titanium dioxide pigment may be used in combination.

In this invention, the following titanium dioxide pigments are preferably used: those coated with various anhydrous or hydrous inorganic oxides (these are disclosed in Japanese Patent Application Kokoku Nos. 44-2564 and 63-11655 and Japanese Patent Application Kokai No. 52-35625); those coated with various organic compounds (these are disclosed in Japanese Patent Application Kokoku Nos. 61-26652 and 59-37304, Japanese Patent Application Kokai Nos. 55-10865, 55-113040, 57-35855, 57-36156, 58-75151, 58-58542, 58-17433, 62-25753, 62-141544, 62-148946 and 62-161147 and GB-1,164,849); other suitable titanium dioxide pigments for photograph (these are shown in Japanese Patent Application Kokai Nos. 57-32442, 57-46818, 58-220140, 59-1544, 59-121329, 59-215344 and 62-103635).

The titanium dioxide pigment content in the resin layer is preferably 5–40% by weight, more preferably 9–30% by weight, most preferably 9–25% by weight. When it is less than 5%, sufficient sharpness and resolving power cannot be obtained. When it is more than 40%, sufficient flowability cannot be obtained.

In order to contain the titanium dioxide pigment in the resin layer of the photographic support, the following two methods are usually employed: The titanium dioxide pigment is previously added to the polyolefin resin at a certain concentration to make a so-called master batch and then it is diluted with a resin for dilution to the desired concentration and the resulting mixture is used as a coating resin. The titanium dioxide pigment is added to the polyolefin resin at the desired concentration to make a so-called compound and it is used as a coating resin.

In order to prepare the master batch and the compound, generally used are a Banbury mixer, a kneader, a kneading extruder, a twin-roll mill, a triple roll mill and the like though a Banbury mixer and a kneading extruder are advantageously used. These mixing machines may be used in combination of two or more. For example, a master batch can be made by the following methods: (1) an antioxidant is added to low-density polyethylene, and to the resulting mixture is added a titanium dioxide pigment, ultramarine, and zinc stearate or magnesium stearate, and then kneaded in a Banbury mixer at an elevated temperature (e.g., 150° C.) to prepare a master batch. (2) A resin composition containing a titanium dioxide pigment without an antioxidant is diluted with a dilution resin to adjust the titanium dioxide content between those of the resin composition and the resin coating. Another method for making a master batch is disclosed in U.S. Pat. No. 4,650,747.

The amount of the fluorescent agent represented by the structural formula [I] contained in the resin layer is preferably 0.1–50 mg/m$^2$, more preferably 0.5–10 mg/m$^2$ considering overall various properties such as whiteness, processability of the resin, anti-bleeding out property, weather resistance and the like.

In order to contain the fluorescent agent of this invention in the resin layer, the following methods are employed: A method of preparing a master batch or compound consisting of a titanium dioxide pigment, the fluorescent, a polyolefin resin and a dispersing agent such as a fatty acid metal salt, in which the fluorescent is added simultaneously with adding the titanium dioxide pigment. A method in which the fluorescent agent is mixed with a low-molecular weight polyolefin which is solid at ordinary temperature and has a lower softening point than the main polyolefin resin and/or a dispersing agent such as a fatty acid metal salt and then the resulting mixture is dispersed in the main polyolefin resin to contain the fluorescent agent in the resin layer.

The film used as a sheet in this invention includes a polyester film, a polystyrene film, a cellulose acetate film, a cellulose acetate butyrate film, a nylon film, a polycarbonate film, a polysulfone film, a polymethylpentene film, a polypropylene film and the like, and a polyester film is preferable. These films may be of an unstretched type, a stretched type or a biaxially oriented type. Multi-layered film of them can also be used. The thickness of the film is preferably 40–400 μm.

As a pulp, for example, there can be used a hardwood pulp whose fibers are fine and short; a bleached hardwood sulphite pulp produced under appropriate conditions; a natural pulp having a weight average fiber length of 0.4–0.9 mm, a number average fiber width of 13.5 μm or more, and a number average fiber thickness of 4 μm or less; a mixture of a softwood pulp and a hardwood pulp. However, if necessary, synthetic pulp or synthetic fiber may be used along with the natural pulp. As the natural pulp, preferably used is a wood pulp such as softwood pulp, hardwood pulp or a mixture thereof, which has been subjected to usual bleaching with chlorine, hypochlorite, chlorine dioxide or the like; alkali extraction or alkali treatment; oxidation bleaching with hydrogen peroxide, oxygen or the like; or a combination of these treatments. Moreover, various pulps may be used such as kraft pulp, sulfite pulp, soda pulp and the like.

Into the base paper used in this invention may be incorporated various sizing agents, high molecular weight compounds or additives in the preparation of a paper slurry.

The sizing agents for the base paper used in this invention include metal salts of fatty acids, fatty acids, alkylketene dimers, alkenyl- or alkyl-succinic anhydrides, epoxidated higher fatty acid amides obtained from a reaction of a higher fatty acid and polyalkylene polyamine, and organic fluoro compounds as disclosed in U.S. Pat. Nos. 2,559,751, 2,567,011, 2,732,398, 2,764,620, 2,806,866, 2,809,998, 2,915,376, 2,915,528, 2,934,450, 2,937,098, 2,957,031, 3,472,894, and 3,555,089. Generally, the organic fluoro compounds are dispersed in an aqueous solution and then added to a paper stock.

The sizing agent suitable for the base paper used in this invention includes metal salts of fatty acids and fatty acids in such a form that they can be fixed to pulp using a water-soluble aluminium salt such as aluminium chloride, sulfite alumina, poly (aluminium chloride) or the like; alkylketene dimers in such a form that they can be fixed with or without the water-soluble aluminium salt and a combination of the alkylketene dimer and an epoxized amide of a higher fatty acid. The metal salts of higher fatty acids and the fatty acids are preferably those having 12–22 carbon atoms and they are preferably added in an amount of 0.5–4.0% by weight based on the bone-dry weight of the pulp. The proportion the solid weight of the water-soluble aluminium salt optionally added to the weight of the sizing agent is preferably 1/20–4/1, more preferably 1/10–1/1. The alkyl group of the alkylketene dimers has preferably 8–30 carbon atoms, more preferably 12–18 carbon atoms. Usually, alkylketene dimers are on the market in the form of an emulsion, and a specific example is Aquapel 360XC (a trade name of Dic Hercules Chemicals. Inc.). They are added preferably in an amount of 0.2–0.4% by weight based on the bone-dry weight of the pulp.

The high molecular weight compound advantageously added to the base paper used in this invention in preparing a paper slurry includes a cationic wet-strength-reinforcing agent or a cationic, anionic or amphoteric strength-reinforcing agent. The cationic wet-strength-reinforcing agent is preferably polyamine-polyamide-epichlorohydrin resin and it is added in an amount of preferably 0.05–4.0% by weight, more preferably 0.15–1.5% by weight, based on the dry weight of the pulp. Specific examples of the cationic wet-strength-reinforcing agent are Kymene 557H, Kymene S-25, Epinox P-130 (these are trade names of Dic Hercules Chemicals. Inc.) and the like.

The cationic, anionic and amphoteric strength-reinforcing agents include cationized starch as disclosed in U.S. Pat. No. 4,665,014; cationic poly(vinyl alcohol) such as a quaternary poly(vinyl alcohol) obtained by a reaction of poly(vinyl alcohol) and a cationizing agent (e.g., 3-chloro-2-hydroxy-propyltrimethyl ammonium chloride); cationic polyacrylamide as disclosed in U.S. Pat. Nos. 4,433,030 and 4,439,496; anionic polyacrylamide such as Polyacron ST-13 (manufactured by Hamano Kagaku Kogyo K.K.) and Polystron 117 (manufactured by Arakawa Kagaku K.K.); amphoteric polyacrylamide such as a copolymer composed of (a) N-vinylpyrazole compound, N-alkylacryloylpiperazine, or N, N-dialkylamino alkylacrylamide, (b) (meth)acrylate, and (c) methacylamide, or composed of acrylamide, acrylic acid, and methylimidazole; vegetable galactomannan such as a natural gum obtained by purifying an albumen of beans of guar or locust, or a derivative obtained by modifying the natural gum; and the like. They are added in an amount of preferably 0.05–8% by weight, more preferably 0.15–4% by weight, based on the dry weight of the pulp.

To the base paper used in this invention may be added various additives in the preparation of the paper slurry. There may be added, in proper combination, a filler such as clay, kaolin, potassium carbonate, barium sulfate, magnesium silicate, titanium dioxide or the like; a pH modifier such as sodium hydroxide, sodium carbonate or the like; a coloring pigment, a coloring dye or a fluorescent whitening agent such as those of stilbene type (e.g. a bis(triazinyl)stilbene disulphonic acid-type), imidazole-type, and cumarin-type.

To the base paper used in this invention may be added various water-soluble polymers, antistatic agents, latices, emulsions, pigments, pH modifiers and the like by spraying or tab size pressing. The water-soluble polymer includes starchy polymers, poly(vinyl alcohol)-type polymers, gelatinic polymers, polyacrylamide-type polymers, cellulosic polymers and the like. The antistatic agent includes alkali metal salts such as sodium chloride, potassium chloride and the like; alkaline earth metal salts such as calcium chloride, barium chloride and the like; colloidal metal oxides such as colloidal silica and the like; organic antistatic agents such as a polymer having structural units of a metal salt of styrenesulphonic acid; and the like. The latices and emulsions include petroleum resin emulsion and latices of styrene/acrylic acid/acrylic acid ester terpolymer, styrene/acrylic acid/butadiene terpolymer, ethylene/vinyl alcohol copolymer, styrene/maleic acid/acrylic acid ester terpolymer and the like. The pigment includes clay, kaolin, talc, barium sulfate, titanium dioxide and the like. The pH modifier includes hydrochloric acid, phosphoric acid, citric acid, sodium hydroxide, sodium carbonate and the like. These additives are advantageously used in appropriate combination with the coloring pigment, coloring dye or fluorescent agent mentioned above.

In order to make the base paper used in this invention, there may be used a conventionally used paper machine such as Fourdrinier machine, a cylinder machine or the like; however, it is advantageous to adopt an appropriate method for making paper as disclosed in U.S. patent application No. 203,619. Though the thickness of the base paper is not critical, the base paper is preferably treated by a calender after the base paper is made. For example, the paper can be hot treated with a calendar at 150°–300° C. under linear pressure of 50–150 kg/cm. The basis weight of the base paper is preferably 40–250 g/m.

The polyolefin resin used in this invention includes homopolymers of olefins such as low-density polyethylene, high-density polyethylene, polypropylene, polybutene, polypentene and the like; copolymers composed of two or more olefins such as ethylene/propylene copolymer and the like; and mixtures thereof. Resins having various densities and melt indexes may be used alone or in admixture. The resin layer may have a multilayer structure composed of, for example, an outermost layer having a melt index (referred to as "MI" hereinafter) of 5–20 and an innermost layer having a MI of 2–10.

The resin layer on the image-forming side of the photographic support of this invention comprises a titanium dioxide pigment, preferably in an amount of 9–20% by weight. However, when the resin layer has a multilayer structure, the innermost layer may or may not contain the titanium dioxide pigment. The polyolefin resin preferably contains the following various additives in appropriate combination: A white pigment such as zinc oxide, talc, calcium carbonate or the like; a fatty acid amide such as stearic acid amide, arachic acid amide or the like; a metal salt of a fatty acid such as zinc stearate, calcium stearate, aluminium stearate, magnesium stearate, zirconium octylate, sodium palmitate, calcium palmitate, sodium laurate or the like; an antioxidant such as tetrakis[methylene-3-(3,5-di-tert-butyl-4-hydroxyphenyl)propionate] methane, 2,6-di-tert-butyl-4-methylphenol or the like; a blue pigment or dye such as cobalt blue, prussian blue, ultramarine blue, cerulean blue, phthalocyanine blue or the like; a magenta pigment or dye such as cobalt violet, fast violet, manganese violet or the like; an ultraviolet absorbing agent such as Tinuvin 320, Tinuvin 326, Tinuvin 328 (trade names of Ciba-Geigy Co. Ltd.) or the like; etc.

The photographic support of this invention is produced by a so-called extrusion coating method, in which molten polyolefin resin is casted on the running sheet to coat both sides of the sheet with the resin. In order to form a resin layer having a multilayer structure, preferably used is a so-called tandem extrusion system, in which the inner resin layer and the outermost resin layer are successively, preferably continuously, formed by extrusion coating or a so-called coextrusion coating system in which the outermost resin layer and the inner resin layer are simultaneously formed by extrusion coating. Before the sheet is coated with the polyolefin resin, the sheet is preferably subjected to an activating treatment such as a corona discharge treatment, a flame treatment or the like. When a film is used as the sheet, the film is preferably subjected to an appropriate treatment such as etching, forming an anchor coat or the like in order to improve the adhesion to the resin layer (e.g. a polyolefin resin layer). When a film (e.g. a polyester film) is subjected to a corona discharge treatment, the treatment should not be excessive because the excessive treatment may deteriorate the adhesion to the resin layer (e.g. a polyolefin resin layer). The emulsion-layer side of the photographic support has a glossy surface, a finely roughened or matte surface to such an extent that it does not affect the gloss of the surface of the photographic paper obtained therefrom or a silky surface. Usually, the back side of the photographic support has a dull surface. The image-forming side or, if necessary, both sides of the photographic support may be subjected to an activating treatment such as a corona discharge treatment, a flame treatment or the like. The photographic support may be further subjected to an undercoating treatment as disclosed in Japanese Patent Application Kokai No. 61-84643 and the like after the activating treatment. The thickness of the resin layer on the image-forming or back side is not critical; however, it is preferably 10–50 $\mu$m.

For the purpose of the prevention of electrification, curling or the like, various backcoats layers may additionally be applied to the photographic support of this invention. The backcoat layers may contain in appropriate combination an inorganic anti-statistic agent, an organic antistatistic agent, a hydrophilic binder, a latex, a hardening agent, a pigment, a surfactant and the like as disclosed in Japanese Patent Application Kokoku Nos. 52-18020, 57-9059, 57-53940, 58-56859; Japanese Patent Application Kokai Nos. 59-214849 and 58-184144; and the like.

After various photograph-constituting layers are formed by coating, the photographic support of this invention can be applied to various uses such as a color photographic paper, a monochromic photographic paper, a phototype-setting photographic paper, a copy photographic paper, a reversal photographic material, a negative and positive photographic material for silver salt dispersion transfer, a positive photographic material for heat development dispersion transfer, a photographic sheet for silver dye bleach, a printing material and the like. When a glossy photographic paper or a photographic paper for silver dye bleach which requires particularly high-grade appearance is used, a polyolefin-coated sheet in which the substrate is a polyester film is advantageously used. The photographic support may have an emulsion layer containing silver chloride, silver bromide, silver iodobromide, silver iodochloride or the like. The photographic emulsion layer containing a silver halide may contain a color coupler to form a silver halide constituting layer having a multilayer structure. The emulsion layer may contain a physical developing nucleus to form a receiving layer for silver salt dispersion transfer. As a binder of these photographic-constituting layers, there may be used a hydrophilic polymer such as poly(vinyl pyrrolidone), poly(vinyl alcohol), a sulfuric acid ester of a polysaccharide or the like in addition to a conventional gelatin. The photographic-constituting layer may contain various additives. For example, there may be contained, in appropriate combination, an optical sensitizing dye such as a cyanine dye, a merocyanine dye or the like; a chemical sensitizer such as a water-soluble gold compound, a sulfur compound or the like; an antifoggant or a stabilizer such as a hydroxytriazolopyrimidine, a mercaptoheterocyclic compound or the like; a hardening agent such as formaldehyde, a vinylsulfone compound, an aziridine compound; an auxiliary agent for coating such as a salt of benzensulfonic acid, sulfosuccinic acid or the like; an anticontaminant such as a dialkylhydroquinone compound or the like; other components such as a fluorescent agent, a dye for improving the sharpness, an antistatic agent, a pH modifier, a fogging agent, or a water-soluble iridium or rhodium compound in the production dispersion of a silver halide.

The photographic material containing a silver halide obtained from the photographic support of this invention is subjected to treatments such as exposure, development, termination, bleach, stabilization and the like as shown in "Photosensitive Materials for Photography and Handling Thereof" by Goro Miyamoto, published by Kyoritsu Shuppan Co. Ltd., Photographic Techniques Course Vol. 2, depending upon the photographic material thereof. Especially, the multilayer silver halide photographic material which is applied to a single bath bleaching treatment after the coloring development may also be applied to a treatment with a color development solution of any main ingredient such as CD-III, CD-IV (these two compounds are products of Kodak Co. Ltd.), Droxychrom (a trade name of May & Bayker Co. Ltd.) or the like. The development solution comprising the main ingredient may contain a development accelerator such as benzyl alcohol, a thallium salt, phenidone or the like. However, the photographic material may also be treated with a development solution which contains substantially no benzyl alcohol. A useful one-bath bleaching-fixing solution is a solution of a metal salt of aminopolycarboxylic acid (e.g. a ferric salt of ethylenediaminetetraacetic acid, propylenediaminetetraacetic acid, etc.). The useful fixing agent is sodium thiosulfate, ammonium thiosulfate or the like. The one-bath bleaching-fixing solution may contain various additives. For example, there may be contained in combination a desilver accelerator (e.g. mercaptocarboxylic acid as disclosed in U.S. Pat. No. 3,512,979, a mercaptoheterocyclic compound as disclosed in Belgian Patent No. 682,426, etc.), an anticontaminant, a pH modifier, a pH buffer, a hardening agent (e.g. magnesium sulfate, aluminium sulfate, potassium alum, etc.), a surfactant and the like. The one-bath bleaching-fixing solution may be used at various pH values though the useful pH range is 6.0–8.0.

The following Examples further illustrate the invention.

EXAMPLE 1

Preparation of
2,2'-(1,4-naphthalenediyl)-bis(5-nonylbenzoxazole)

(1) Preparation of 2-nitro-4-nonylphenol 10 g of 4-nonylphenol (manufactured by Tokyo Kasei K.K., containing 10% of ortho compound) was dissolved in 30 ml of acetic acid and to the resulting solution was added 20 ml of 30% solution of nitric acid at 5°–10° C. for 2 hours. After 10 minutes, the resulting solution was treated with 50 g of ice water and then extracted with three 50-ml portions of ether. The ether was distilled off and then the residue was isolated using a silica gel column to obtain 9.33 g of the desired product in a 78% yield.

(2) Preparation of 2-amino-4-nonylphenol 5 g of 2-nitro-4-nonylphenol obtained in (1) above was dissolved in 200 ml of THF and reduced with hydrogen at ordinary temperature and ordinary pressure in the presence of Raney nickel for 12 hours until the hydrogen absorption was stopped. After the reaction, the catalyst was removed and most of THF was distilled off to obtain 7.88 g of the desired product (the solvent cannot completely distilled off).

(3) Preparation of
2,2'-(1,4-naphthalenediyl)-bis(5-nonylbenzoxazole)

7.88 g of 2-amino-4-nonylphenol obtained in (2) above (containing the solvent quite a little) was added with 4.29 ml of dimethylaniline to a solution of naphthalene-1,4-dicarboxylic dichloride in chlorobenzene prepared from 1.83 g (8.46 mmol.) of naphthalene-1,4-dicarboxylic acid (manufactured by Pfaltz & Bauer Inc.,) and thionyl chloride. The resulting mixture was subjected to reaction at 90° C. for 2 hours. The reaction mixture was cooled, extracted with hexane and then concentrated to obtain 5.20 g of an amide compound.

To 5.20 g of the amide compound thus obtained were added 15 ml of trichlorobenzene and 0.1 g of zinc chloride and the resulting mixture was subjected to reaction with stirring at 210° C. for 5 hours. After the reaction, the reaction mixture was extracted with water to obtain 4.06 g of a dibenzoxazole derivative. 3.09 g of the dibenzoxazole derivative thus obtained was isolated by a silica-gel column to obtain 2.40 g of a viscous, yellowish-brown solid.

The melting point of this solid was 49°–84° C.

The results of measuring $^1$H-NMR were as follows:

$\delta$(ppm): $\left.\begin{array}{c}0.3\\1.5\end{array}\right\}$ m 38H (—CH)

$\left.\begin{array}{c}7.3\\7.8\end{array}\right\}$ m 8H (benzene or naphthalene nucleus)

8.5 s 2H
9.6 s 2H

EXAMPLE 2

Preparation of
2,2'-(1,4-naphthalenediyl)-bis(5-dodecylbenzoxazole)

(1) Preparation of 4-dodecylphenol 16.75 g of dodecyl chloride was dropwise added to 7.0 g of phenol and the resulting mixture was subjected to reaction at 90° C. for 30 minutes. And then, 12.0 g of AlCl$_3$ powder was added thereto and the resulting mixture was further subjected to reaction at 100° C. for 4 hours. The reaction mixture was cooled and added to dilute hydrochloric acid. The resulting mixture was then subjected to extraction with two 50-ml portions of ethyl acetate. To the resulting solution of the reaction product in the ethyl acetate was added 80 ml of 3% aqueous sodium hydroxide solution, and the aqueous layer was then separated. To the aqueous layer was added conc hydrochloric acid to adjust the pH to 2, and the crystal, thus precipitated was filtered and washed with water to obtain 9.35 g of 4-hydroxyphenyl undecyl ketone. Subsequently, 8.0 g of the 4-hydroxyphenyl undecyl ketone thus obtained was mixed with 650 mg of a 5% active carbon-supported palladium and 100 ml of acetic acid, and the resulting mixture was subjected to reaction in a hydrogen gas stream at 50° C. for 15 hours to reduce the ketone. The reaction mixture was cooled and filtered, and acetic acid was distilled off to obtain 7.50 g of white, solid 4-dodecylphenol.

(2) Preparation of 4-dodecyl-2-nitrophenol 7.5 g of the 4-dodecylphenol obtained in (1) above was dissolved in 25 ml of acetic acid and 12.6 ml of 30% aqueous nitric acid solution was dropwise added slowly to the resulting solution, and then the resulting mixture was subjected to reaction at about 10° C. for one hour. The reaction mixture was added to 35 g of ice water and the extraction with 35 ml of diethyl ether was conducted three times. The diethyl ether layer thus obtained was washed with 35 ml of 5% aqueous NaHCO solution, and then dried with $MgSO_4$. Subsequently, the solvent was distilled off to obtain 5.93 g of 4-dodecyl-2-nitrophenol.

(3) Preparation of 4-dodecyl-2-aminophenol 5.80 g of the 4-dodecyl-2-nitrophenol obtained in (2) above was mixed with 500 mg of 5% active carbon-supported palladium, and 150 ml of tetrahydrofuran and the resulting mixture was contacted with hydrogen at room temperature for 7 hours to reduce the nitro group. The reaction mixture was filtered, and then the solvent was distilled off to obtain 5.21 g of 4-dodecyl-2-aminophenol.

(4) Preparation of 2,2'-(1,4-naphthalenediyl)-bis(5-dodecylbenzoxazole)

5.21 g of the 4-dodecyl-2-aminophenol obtained in (3) above was dissolved in a mixture of 4.8 ml of dimethylaniline and 50 ml of chlorobenzene, and thereto was added 20 ml of a chlorobenzene solution of 1,4-naphthalenedicarbonyl dichloride prepared from 2.05 g of 1,4-naphthalenedicarboxylic acid (manufactured by Pfaltz & Bauer Inc.,). The resulting mixture was subjected to reaction at 100° C. for 3 hours, and then cooled. To the reaction mixture were added 400 ml of methanol and 85 ml of 2N HCl to precipitate the reaction product.

The reaction product thus obtained was filtered, washed with 170 ml of 2N HCl, further washed with 36 ml of methanol, and then dried. Thereto were added 200 mg of $ZnCl_2$ and 19 ml of trichlorobenzene, and the resulting mixture was stirred at 210° C. for 3 hours to distil off the water produced. The resulting mixture was cooled and dissolved in a mixture of 125 ml of dimethyl formamide and 11 ml of trichlorobenzene. To the resulting solution was added 55 ml of methanol to precipitate the objecting compound. The precipitate was filtered and washed with methanol to obtain 4.65 g of 2,2'-(1,4-naphthalenediyl)-bis(5-decylbenzoxazole).

The melting point of this compound was 88°-96° C.
The results of measuring $^1$H-NMR were as follows:

| $\delta$ (ppm): | | | |
|---|---|---|---|
| 0.85–0.90 | t | 6H | (—$CH_3$) |
| 1.26–1.33 | m | 36H | (—$CH_2$—) |
| 1.60–1.70 | m | 4H | (—$CH_2$—) |
| 2.73–2.80 | m | 4H | (—$CH_2$—) |
| 7.22–7.26 | d | 2H | (benzene nucleus) |
| 7.26–7.58 | d | 2H | (benzene nucleus) |
| 7.69 | d | 2H | (benzene nucleus) |
| 7.76–7.80 | m | 2H | (naphthalene nucleus) |
| 8.49 | s | 2H | (naphthalene nucleus) |
| 9.57–9.61 | m | 2H | (naphthalene nucleus) |

The results of the elemental analysis are shown below.

| | C | H | N |
|---|---|---|---|
| Calculated % | 82.47 | 8.94 | 4.01 |
| Found % | 81.83 | 8.98 | 3.94 |

EXAMPLE 3 AND COMPARATIVE EXAMPLES 1–8

(1) Preparation of base paper

A mixture of 50 parts by weight of bleached hardwood kraft pulp and 50 parts by weight of softwood sulfite pulp was beaten until it had 310 ml of Canadian standard freeness. And then, to 100 parts by weight of the pulp mixture were added 3 parts by weight of cationized starch, 0.2 part by weight of anionized polyacrylamide, 0.4 part by weight (as ketene dimers content) of an alkylketene dimer emulsion and 0.4 part by weight of a polyamide-polyamine-epichlorohydrin resin. From the resulting mixture, paper having a basis weight of 160 g/$m^2$ was prepared and then the wet paper thus obtained was dried at 110° C. Subsequently, the paper was impregnated with a soaking solution consisting of 3 parts by weight of carboxy-modified poly(vinyl alcohol), 0.05 part by weight of a fluorescent agent, 0.002 part by weight of a blue dye, 0.2 part by weight of citric acid and 97 parts by weight of water in a proportion of 25 g/$m^2$. The impregnated paper was dried with heat air at 110° C. and then treated by a calender at a linear pressure of 90 kg/cm. Further, both sides of the paper were treated by corona discharge to obtain a paper substrate for a resin-coated paper type photographic support.

(2) Preparation of a photographic support

A mixture of a high-density polyethylene (density: 0.96 g/$cm^3$, MI: 5) and a low-density polyethylene (density: 0.92 g/$cm^3$, MI: 5) at a weight ratio of 1:1 was melt-extruded at a resin temperature of 330° C. and the back side of the base paper obtained in (1) above was coated with the molten mixture by a coating machine so that the coated layer had a thickness of 30 μm. And then, each of the resin compositions shown in Table 1 was stirred enough and the image-forming side of the base paper was coated with the resin composition at a resin temperature of 320° C. by a screw type extrusion machine having an extruder bore of 65 mm and a melt extrusion machine having a 75-mm-wide T-die so that the coated layer had a thickness of 30 μm to produce the desired photographic support containing the titanium dioxide pigment and the like. The photographic support thus obtained was processed so that the resin layer on the image-forming side containing the titanium dioxide pigment and the like had a smooth and grossy surface and the resin layer on the back side had a paper-like matte surface. In Table 1, the figures are parts by weight and % is also by weight (the same applies to the other Tables).

TABLE 1

| Master batch | | | Resin for |
|---|---|---|---|
| A[*1] | B[*2] | Resin containing a fluorescent agent | dilution[*4] |

TABLE 1-continued

| | | | | |
|---|---|---|---|---|
| Comparative Example 1 | 24 | 6 | — | 70 |
| Comparative Example 2 | 20 | 10 | — | 70 |
| Comparative Example 3 | 30 | — | A resin*3 containing 10% of cobalt blue #3*5 and 0.5% of zinc stearate 2 | 68 |
| Comparative Example 4 | 30 | — | A resin*3 containing 0.1% of cromophthal blue A3R*6 and 0.1% of low-molecular weight polyethylene 2 | 68 |
| Comparative Example 5 | 24 | 6 | A resin*3 containing 2% of the fluorescent agent of the structural formula [XI] 5 | 65 |
| Comparative Example 6 | 24 | 6 | A resin*3 containing 0.4% of the fluorescent agent of the structural formula [XII] and 0.4% of low-molecular weight polyethylene 10 | 60 |
| Comparative Example 7 | 24 | 6 | A resin*3 containing 0.1% of the fluorescent agent of the structural formula [XIII] and 0.1% of low-molecular weight polyethylene 10 | 60 |
| Comparative Example 8 | 24 | 6 | A resin*3 containing 0.1% of the fluorescent agent XIV and 0.1% of low-molecular weight polyethylene 10 | 60 |
| Example 3 | 24 | 6 | A resin*3 containing 0.1% of the fluorescent agent III and 0.1% of low-molecular weight polyethylene 10 | 60 |

Note:
Structural formula [XI]

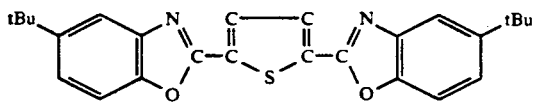

Structural formula [XII]

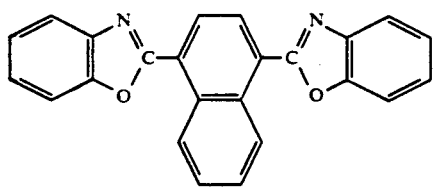

Structural formula [XIII]

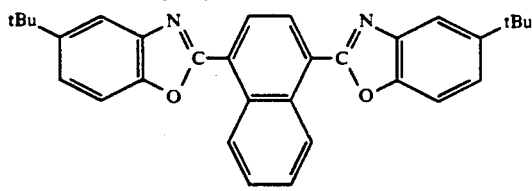

Structural formula [XIV]

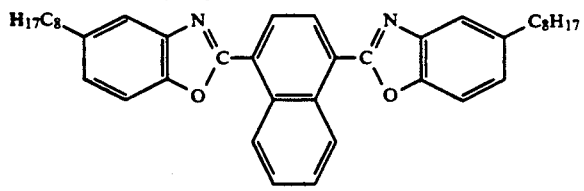

*1 A master batch consisting of 50 parts by weight of rutile type titanium dioxide, 2.5 parts by weight of zinc stearate and 47.5 parts by weight of polyethylene having a density of 0.918 and a MI of 9,
*2 A master batch consisting of 50 parts by weight of rutile type titanium dioxide, 1.25 parts by weight of ultramarine blue, 2.5 parts by weight of zinc stearate and 46.25 parts by weight of polyethylene having density of 0.918 and a MI of 9,
*3 Polyethylene having a density of 0.918 and a MI of 9,
*4 Polyethylene having a density of 0.92 and a MI of 5,
*5 Manufactured by The Shepard Color Company,
*6 Cromophthal blue A3R (manufactured by Ciba-Geigy Corp.) having the following TABLE 1-continued structure:

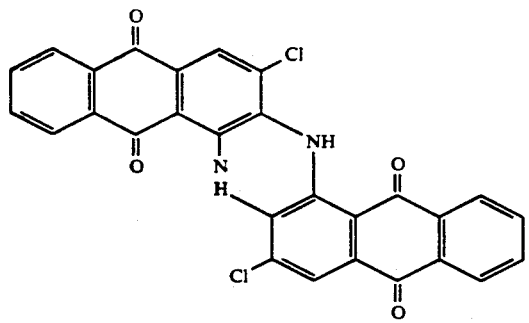

(3) Evaluation of the photographic support

A part of each of the photographic supports thus obtained was prepared in the form of a monochromic photographic paper. The other part was coated with gelatin in the same proportion as contained in the above monochromic photographic paper. These samples were evaluated as follows.

(a) Whitening effect: The color of the samples coated with gelatin was visually observed. "○" represents white. "Δ" represents slightly yellow. "x" represents yellow.

(b) Resistance to a treatment solution: The monochromic photographic paper was treated with an acidic hardening-fixing solution (Kodak priscription F-5) at 20° C. for 5 minutes and then washed with water. The color of the surface was compared with the untreated gelatin-coated samples. "○" represents that no change was recognized. "Δ" represents that yellowing was slightly recognized. "x" represents that yellowing was recognized.

(c) Discoloration in darkness: The samples coated with gelatin were preserved in a dark place at 50° C. for a week and then the color of each of the samples was compared with that before the preservation. "○", "Δ" and "x" represent respectively the same as shown in (b) above.

(d) Discoloration by sunlight: The samples coated with gelatin were exposed to sunlight for two months and then the color of each of the samples was compared with that before the preservation. "○", "Δ" and "x" represent respectively the same as shown in (b) above.

(e) Bleeding out property: Upon the image-forming side of each of the samples which were not coated with gelatin was put a grossy side of non-fluorescent, resin-coated paper and the resulting assembly was preserved under a load of 50 $g/cm^2$ at 50° C. for 3 days. Thereafter, the side of the non-fluorescent resin-coated paper which side had been contacted with the image-forming side of the sample was irradiated with ultraviolet rays and the color of the irradiated portion was observed. "○" represents that no fluorescence was observed. "Δ" represents that fluorescent was partially observed on account of the migration of a small amount of the fluorescent agent. "x" represents that fluorescent was observed overall on account of the migration of most of the fluorescent agent. The results are shown in Table 2.

TABLE 2

| | | | Color change | | | |
|---|---|---|---|---|---|---|
| | Whitening effect | Remarks | Resistance to treatment solution | Discoloration in darkness | Discoloration by sunlight | Bleeding out property |
| Comparative Example 1 | x | | o | o | o | o |
| Comparative Example 2 | o | Low brightness | o | o | o | o |
| Comparative Example 3 | o | Low brightness | o | o | o | o |
| Comparative Example 4 | o | Low brightness | o | o | o | o |
| Comparative Example 5 | o | Clearly white | x | x | x | x |
| Comparative Example 6 | o | Clearly white | o | o | o | x |
| Comparative Example 7 | o | Clearly white | o | o | o | x |
| Comparative Example 8 | o | Clearly white | o | o | o | Δ |
| Example 3 | o | Clearly white | o | o | o | o |

In Comparative Examples 2-4, in which the color was compensated by the coloring pigments, the brightness is low and dull is appreciated. In Comparative Example 5, the whiteness is clear the resistance to a treatment solution, the preservability and the bleeding out property are inferior. In Comparative Examples 6, 7 and 8, the bleeding out property is inferior. Incidently, in Comparative Example 2, accumulation of the composition in the form of an icicle was caused at the die lip opening.

EXAMPLES 4-6 AND COMPARATIVE EXAMPLES 9-10

The same procedure as in Example 3 was repeated, except that the modifications shown in Table 3 were made.

TABLE 3

| | Master batch | | | Resin for dilution | |
|---|---|---|---|---|---|
| | A*7 | B*8 | Resin containing a fluorescent agent | *9 | *10 |
| Comparative Example 9 | 20 | 10 | — | 45 | 25 |
| Comparative Example 10 | 20 | 10 | A resin*11 containing 1% of Daiichi Pink DP-3*12<br>10 | 35 | 25 |
| Example 4 | 24 | 6 | A resin*11 containing 0.1% of the fluorescent agent III and 0.1% of low-molecular weight polyethylene<br>10 | 35 | 25 |
| Example 5 | 30 | — | A resin*11 containing 0.1% of the fluorescent agent III and 0.1% of low-molecular weight polyethylene<br>10<br>A resin*11 containing 0.1% of Cromophthal blue A3R*13<br>1.5 | 33.5 | 25 |
| Example 6 | 30 | — | A resin*11 containing 0.1% of the fluorescent agent III and 0.1% of low molecular weight polyethylene<br>10<br>A resin*11 containing 0.1% of Cromophthal blue A3R*13<br>1.5<br>A resin*11 containing 0.1% of Hostaperm pink E*14 and 0.1% of low-molecular weight wax<br>0.5 | 33 | 25 |

Note
*7A master batch consisting of 50 parts by weight of rutile type titanium dioxide coated with alumina in an alumina-coating proportion (to titanium dioxide) of 0.5% (as $Al_2O_3$), 2.5 parts by weight of zinc stearate and 47.5 parts by weight of polyethylene having a density of 0.918 and a MI of 9.
*8A master batch consisting of 50 parts by weight of the rutile type titanium dioxide mentioned above, 1.25 parts by weight of ultramarine blue, 2.5 parts by weight of zinc stearate and 46.25 parts by weight of the polyethylene mentioned above.
*9Polyethylene having a density of 0.92 and a MI of 5.
*10Polyethylene having a density of 0.96 and a MI of 7.
*11The same as *3 in Table 1.
*12Ultramarine blue manufactured by Daiichi Kasei Kogyo K.K.
*13The same as *6 in Table 1.
*14A quinacridonic magenta pigment manufactured by Hoechst AG.

A part of each of the photographic support obtained was coated with a blue-sensitive emulsion layer containing a yellow-coloring coupler, an intermediate layer, a green-sensitive emulsion layer containing a magenta-coloring coupler, an ultraviolet-absorptive layer containing an ultraviolet absorber, a red-sensitive emulsion layer containing a cyan-coloring coupler and a protective layer in this order to obtain a color photographic paper. The other part was coated with gelatin in the same proportion as in the color photographic paper.

The same evaluation as in Example 3 was repeated, except that non-exposed color photographic paper was treated with a color developing solution and a bleaching-fixing solution, these having the following composition, (treatment period: coloring development; 210 seconds, bleaching-fixing; 90 seconds, washing with water; 210 seconds, treatment temperature: 33° C.) instead of the acidic hardening-fixing solution used in the evaluation of the resistance to a treatment solution in Example 3. The results are shown in Table 4.

| Color developing solution | |
|---|---|
| Sodium carbonate monohydrate: | 46.0 g |
| Anhydrous sodium sulfite: | 2.0 g |
| Potassium bromide: | 0.5 g |
| CD-III: | 4.5 g |
| Sodium hexametaphosphate: | 0.5 g |
| Hydroxylamine sulfate: | 2.0 g |
| Fluorescent whitening agent: | 0.5 g |
| Benzyl alcohol: | 12 cc |
| Diethylene glycol: | 10 cc |

Water was added to the mixture thereof to make the total amount 1 liter and then sodium hydroxide was added to adjust the pH to 10.2.

| Bleaching-fixing solution | |
|---|---|
| Ferric complex salt of ethylenediaminetetraacetic acid: | 56 g |
| Disodium salt of ethylenediaminetetraacetic acid: | 2 g |
| Ammonium thiosulfate: | 60 g |
| Anhydrous sodium sulfite: | 20 g |
| Acidic sodium sulfite: | 5 g |
| Disodium phosphate: | 12 g |

Water was added to the mixture thereof to make the total amount 1 liter.

TABLE 4

| | Whitening effect | Remarks | Color change | | | Bleeding out property |
| --- | --- | --- | --- | --- | --- | --- |
| | | | Resistance to treatment solution | Discoloration in darkness | Discoloration by sunlight | |
| Comparative Example 9 | o | Low brightness | o | o | o | o |
| Comparative Example 10 | o | Low brightness | o | o | o | o |
| Example 4 | o | Clearly white | o | o | o | o |
| Example 5 | o | Clearly white | o | o | o | o |
| Example 6 | o | Clearly white | o | o | o | o |

Comparative Examples 9 and 10 show no color but show low brightness. Examples 4-6 show clear whiteness and show no color change or bleeding out.

EXAMPLES 7-13

The same procedure as in Example 4 was repeated, except that the modifications shown in Table 5 were made to prepare a photographic support, and then the same was evaluated. The results are shown in Table 6.

TABLE 5

| | Master batch | | Resin containing a fluorescent agent | Resin for dilution | |
| --- | --- | --- | --- | --- | --- |
| | A*15 | B*16 | | *18 | *19 |
| Example 7 | 24 | 6 | A resin*17 containing 0.01% of the fluorescent agent III and 0.01% of a low-molecular weight wax 1 | 44 | 25 |
| Example 8 | 24 | 6 | A resin*17 containing 0.01% of the fluorescent agent III and 0.01% of a low-molecular weight wax 3 | 42 | 25 |
| Example 9 | 24 | 6 | A resin*17 containing 0.1% of the fluorescent agent III and 0.1% of a low-molecular weight wax 1 | 44 | 25 |
| Example 10 | 24 | 6 | A resin*17 containing 0.1% of the fluorescent agent III and 0.1% of a low-molecular weight wax 3 | 42 | 25 |
| Example 11 | 24 | 6 | A resin*17 containing 0.1% of the fluorescent agent III and 0.1% of a low-molecular weight wax 10 | 35 | 25 |
| Example 12 | 24 | 6 | A resin*17 containing 1% of the fluorescent agent III and 1% of a low-molecular weight wax 3 | 42 | 25 |
| Example 13 | 24 | 6 | A resin*17 containing 1% of the fluorescent agent III and 1% of a low-molecular weight wax 10 | 35 | 25 |

Note:
*15 The same as *7 in Table 3.
*16 The same as *8 in Table 3.
*17 The same as *3 in Table 1.
*18 The same as *9 in Table 3.
*19 The same as *10 in Table 3.

TABLE 6

| | Whitening effect | Remarks | Color change | | | Bleeding out property |
| --- | --- | --- | --- | --- | --- | --- |
| | | | Resistance to treatment solution | Discoloration in darkness | Discoloration by sunlight | |
| Example 7 | X-Δ | Yellow (little whitening effect is observed) | O | O | O | O |
| Example 8 | X-Δ | Yellow (little | O | O | O | O |

TABLE 6-continued

| | Whitening effect | Remarks | Color change | | | |
|---|---|---|---|---|---|---|
| | | | Resistance to treatment solution | Discoloration in darkness | Discoloration by sunlight | Bleeding out property |
| | | whitening effect is observed) | | | | |
| Example 9 | Δ | Slightly yellow | ○ | ○ | ○ | ○ |
| Example 10 | ○ | Clearly white | ○ | ○ | ○ | ○ |
| Example 11 | ○ | Clearly white | ○ | ○ | ○ | ○ |
| Example 12 | ○ | Clearly white (the same as in Example 12) | ○ | ○ | ○ | ○ |
| Example 13 | Δ | Slightly yellow | ○ | ○ | ○ | ○ |

As shown in Table 6, sufficient whitening effects cannot be obtained when the amount of the fluorescent agent is too small or too large.

EXAMPLE 14

The same procedure as in Example 4 was repeated, except that the fluorescent agent V was used instead of the fluorescent agent III used in Example 4. The results obtained are shown in Table 7 in which Example 4 is also shown for comparison.

TABLE 7

| | Whitening effect | Remarks | Color change | | | |
|---|---|---|---|---|---|---|
| | | | Resistance to treatment solution | Discoloration in darkness | Discoloration by sunlight | Bleeding out property |
| Example 4 | ○ | Clearly white | ○ | ○ | ○ | ○ |
| Example 14 | ○ | Clearly white | ○ | ○ | ○ | ○ |

Furthermore, the samples of Examples 4 and 14 were cut into 5 cm (MD)×50 cm (CD) pieces. As to each of Examples 4 and 14, 40 pieces were prepared, and they were heated at 50° C. for 48 hours. And then, the resin layer of each piece was peeled off and the ratio of the damaged area of the paper was measured, which indicates the adhesion to the resin layer. The ratios obtained as to Examples 4 and 14 were 38% and 45% respectively, which shows that the fluorescent agent V is superior in anti-bleeding out property to the fluorescent agent III because the former has a longer alkyl group as substitutent than the latter.

EXAMPLES 15 AND 16

The same procedure as in Example 4 was repeated, except that in the preparation of the titanium dioxide masterbatch, the fluorescent agent III or V was added without adding the low molecular weight polyethylene used in Example 4. The same results as in Example 4 were obtained.

EXAMPLE 17

The same procedure as in Example 4 was repeated, except that anatase type titanium dioxide was used instead of the rutile type titanium dioxide used in Example 4.

The same results as in Example 4 were obtained, except that the yellowness was not so distinctive even in the absence of the fluorescent agent and further clear whiteness was obtained by using the fluorescent agent.

EXAMPLE 18

The same procedure as in Example 4 was repeated, except that the fluorescent agent IV or VIII was used instead of III used in Example 4. The same results as in Example 4 were obtained.

What is claimed is:

1. A fluorescent agent for polyolefin resins, consisting of an alkyl-substituted 2,2'-(1,4-naphthalenediyl)-dibenzoxazole represented by the structural formula (I):

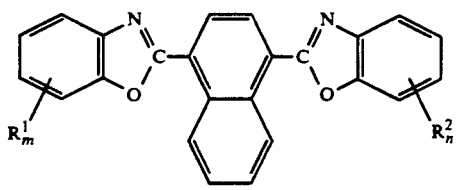

[I]

wherein $R^1$ and $R^2$ are the same alkyl groups which are straight chain and/or branched alkyl groups each having 9-20 carbon atoms, and are attached to the 5- or 7-position of the benzoxazole ring, and m and n are 1.

2. An alkyl-substituted 2,2'-(1,4-naphthalenediyl)-dibenzoxazole according to claim 1, wherein $R^1$ and $R^2$ are the same alkyl groups having 9-16 carbon atoms, and m and n are the same positive integers.

3. An alkyl-substituted 2,2'-(1,4-naphthalenediyl)-dibenzoxazole according to claim 2, wherein m and n are 1.

4. An alkyl-substituted 2,2'-(1,4-naphthalenediyl)-dibenzoxazole according to claim 1, wherein each of $R^1$ and $R^2$ is a nonyl group and attached to the 5- or 7-position of the benzoxazole ring, and m and n are 1.

5. An alkyl-substituted 2,2'-(1,4-naphthalenediyl)-dibenzoxazole according to claim 1, wherein each of $R^1$ and $R^2$ is a dodecyl group and attached to the 5- or 7-position of the benzoxazole ring, and m and n are 1.

* * * * *